(12) United States Patent
Scheuch et al.

(10) Patent No.: US 6,343,602 B1
(45) Date of Patent: Feb. 5, 2002

(54) METHOD OF AND A DEVICE FOR DRY APPLICATION OF SUBSTANCES ON INHALABLE PULVERULENT CARRIER SUBSTANCES

(75) Inventors: Gerhard Scheuch, Gemünden; Knut Sommerer, München, both of (DE)

(73) Assignee: GSF Forshungszentrum fur Umwelt und Ges, Obersshleibheim (DE)

( * ) Notice: Subject to any disclaimer, the term of this patent is extended or adjusted under 35 U.S.C. 154(b) by 0 days.

(21) Appl. No.: 09/549,166

(22) Filed: Apr. 13, 2000

(30) Foreign Application Priority Data

Apr. 16, 1999 (DE) .......................................... 199 17 347

(51) Int. Cl.$^7$ .............................................. A61M 15/00
(52) U.S. Cl. ............................ 128/203.15; 128/203.12; 128/200.14
(58) Field of Search ...................... 128/203.15, 203.12, 128/200.14, 200.21; 239/338

(56) References Cited

U.S. PATENT DOCUMENTS

| 4,057,616 | A | | 11/1977 | Wolfangel | |
|---|---|---|---|---|---|
| 4,649,911 | A | * | 3/1987 | Knight et al. | 125/200.21 |
| 5,320,108 | A | * | 6/1994 | Cloutier | 128/716 |
| 5,382,434 | A | | 1/1995 | de Haan et al. | |
| 5,458,135 | A | * | 10/1995 | Patton et al. | 125/200.14 |
| 5,709,202 | A | * | 1/1998 | Lloyd et al. | 128/200.14 |
| 5,826,633 | A | * | 10/1998 | Parks et al. | |
| 5,829,436 | A | | 11/1998 | Rubsamen et al. | |
| 5,873,358 | A | * | 2/1999 | Gonda et al. | 128/200.14 |

FOREIGN PATENT DOCUMENTS

WO        98/36888        8/1998

* cited by examiner

Primary Examiner—John G. Weiss
Assistant Examiner—V. Srivastava
(74) Attorney, Agent, or Firm—Sughrue Mion, PLLC

(57) ABSTRACT

For maintaining the inhalable pulverulent carrier substances and their properties when marker substances and/or active substances are applied, initially the substance to be applied is dissolved in a liquid, then the fluid is vaporized and finally the aerosol droplets are dried for forming aerosol particles whereupon the aerosol particles are whirled for being contacted with the pulverulent substance. The associated device comprises an aerosol generator 11 including on the nozzle-type, ultrasonic or other vaporizer for the substance to be applied, which is dissolved in a liquid, and a drying means for drying the aerosol particles so formed. Moreover, a mixing chamber 12 is provided for receiving pulverulent carrier substance and for establishing a whirling contact thereof with dry aerosol particles circulated and introduced therein.

22 Claims, 4 Drawing Sheets

FIG. 6

```
┌─────────────┐            ┌─────────────┐
│   SUPPLY    │─S1         │   SUPPLY    │─S2
│ PULVERULENT │            │MARKER/ACTIVE│
│   CARRIER   │            │  SUBSTANCE  │
└─────────────┘            └──────┬──────┘
       │                          ▼
       │                   ┌─────────────┐
       │                   │   DISSOLVE  │─S3
       │                   │ SUBSTANCE IN│
       │                   │    LIQUID   │
       │                   └──────┬──────┘
       │                          ▼
       │                   ┌─────────────┐
       │                   │   VAPORIZE  │─S4
       │                   │    LIQUID   │
       │                   └──────┬──────┘
       │                          ▼       ◄───┐
       │                   ┌─────────────┐    │
       │              S5 ─ │   DRY TO    │    │
       │                   │   PRODUCE   │    │
       │                   │  PARTICLES  │    │
       │                   └──────┬──────┘    │
       │              S6          ▼           │
       │                       ◇ MOISTURE ◇   │
       │                       ◇  LEVEL   ◇──NO
       │                       ◇   OK?    ◇
       │                          │YES
       │                          ▼
       │                   ┌─────────────┐
       └──────────────────►│  ESTABLISH  │
                           │   WHIRLING  │
                           │   CONTACT   │
                           └──────┬──────┘
                                  ▼
                                ┌───┐
                                │END│
                                └───┘
```

METHOD OF AND A DEVICE FOR DRY APPLICATION OF SUBSTANCES ON INHALABLE PULVERULENT CARRIER SUBSTANCES

FIELD OF THE INVENTION

The present invention relates to a method of and a device for dry application of substances, particularly marker substances and/or active substances, on inhalable pulverulent carrier substances.

BACKGROUND OF THE INVENTION

Inhalable dry powders are partly made of lactose, liposomes or other carrier substances. For checking the quantity of particles deposited in the lung it has been known to apply a marker on these pulverulent carrier substances or aerosol particles, respectively, which can be established in terms of position and distribution from outside the lung. To this end, normally radioactive substances such as sodium pertechnetate (99mTc) Tc04 are used. Beyond that, however, it will also be possible in the future to use magnetic markers or contrast media which can be detected by means of nuclear magnetic resonance spectrography (NMR). It is also possible to apply minute quantities of active substances, especially medicaments, on pulverulent inhalable carrier substances, instead of this marker of pulverulent carrier substances for the external detection of the quantities of particles which have been deposited in the lung. Moreover, the application of such active substances in small quantities may be combined with a marker.

So far, it is not yet known to apply marker substances and/or active substances on inhalable pulverulent carrier substances in a dry form. It is common to introduce the small particles of the pulverulent carrier substance into a solution in which the marker substance is contained and then dried. This entails the inexpedient problem that particularly with water-soluble substances or carrier substances, respectively, the properties of the carrier substance particles are lost or that these particles dissolve completely.

SUMMARY OF THE INVENTION

The invention is now based on the problem of rendering a method and a device of the type available which has been outlined by way of introduction, wherein the conservation of the inhalable pulverulent carrier substances and their properties is achieved when marker substances and/or active substances are applied.

In accordance with the invention this problem is solved in terms of a method by the features defined in Patent Claim 1. Preferred features constituting an expedient improvement of this method are defined in the dependent method claims 2 to 5.

This problem is solved in terms of a device by the features defined in Patent claim 6. Preferred further embodiments of the invention are defined in the dependent device claims.

In accordance with the inventive method, as illustrated in FIG. 6, the dry application of substances provided in step S1 on inhalable pulverulent carrier substances is realized by provided in step S2 by initially dissolving the substance to be applied to a liquid in step S3, by subsequently vaporizing the fluid in step S4, and by drying the aerosol droplets to so formed completely for generating aerosol particles in step S5. Then a whirling contact to the aerosol particles with the pulverulent carrier substance is established in step S7, with the fine aerosol particles expediently adhering to the particles to be marked.

In accordance with a preferred embodiment of the invention, the moisture of the aerosol particles is controlled prior to the whirling contact in step S7, so as to avoid any influence on the power particles to be marked in the pulverulent carrier substances, with the moisture of the aerosol particles being preferably checked in step S6 and subject to further vaporization until the moisture is adapted tot he respective carrier substance.

In correspondence with a preferred embodiment of the inventive method, the whirling contact is realized by aspiration of circulated aerosol particles through the carrier substance, with the aspiration of the aerosol particles being preferably performed via a retaining filter. In this manner, the pulverulent carrier substance is whirled up expediently, and due to the circulated aerosol particles, which are transferred in a manner similar to that in a cyclone separator, a particularly intimate mixing and the desired dry application of the marker substances and/or active substances is achieved.

According to the inventive device an aerosol generator and a mixing chamber are provided as apparatus elements, with the aerosol generator comprising a nozzle vaporizer for the substance to be applied and dissolved in a liquid, as well as a means for drying the aerosol particles so formed. The mixing chamber serves to receive pulverulent carrier substance and to establish the whirling with dry aerosol particles introduced by circulation.

The substance, for instance sodium per-technetate, which is to be used for marking the pulverulent carrier substances, is dissolved in a liquid such as water or alcohol, with vaporization taking place in the aerosol generator by means of a conventional jet-type or ultrasonic vaporizer. The vaporization may be performed with any system whatsoever which permits the formation of an aerosol from a liquid. The aerosol generator has expediently a large volume and contains a desiccant such as silica gel, for drying the aerosol droplets generated completely before they leave the aerosol generator. In this manner it is possible to produce very small aerosol particles having a particle size in the range from 1 nm to 500 nm.

These dry aerosol particles are then introduced into the joining mixing chamber where the inhalable pulverulent carrier substance is contained on which the dry aerosol particles are to be applied.

For the introduction of dry aerosol particles and for whirling in the mixing chamber a vacuum pump is provided in correspondence with a preferred embodiment, which pump is connected to the mixing chamber via a filter array. Due to the eccentric introduction of the dry aerosol particles into the mixing chamber that is preferably provided in the lower region of the mixing chamber with an oblique downward orientation, which is moreover expediently provided, the inhalable pulverulent carrier substance is whirled up and the fine aerosol particles adhere to the pulverulent particles of the carrier substance.

For checking the moisture of the dried aerosol particles preferably a moisture sensor is provided, particularly a hygrometer, which moisture sensor is preferably disposed in a connecting line between the aerosol generator and the mixing chamber, and preferably the moisture of the dried aerosol particles can be adjusted for adaptation to the respective carrier substance by means of an appropriate on/off operation of the nozzle-type vaporizer in the aerosol generator.

In accordance with another preferred embodiment of the invention, the mixing chamber is adapted to be closed and sealed by means of a cover including an opening connector for the connection of a vacuum pump, with the cover being adapted for being partly inserted into an upper section of the mixing chamber and for being fastened on the mixing chamber by means of a swivel nut. With these provisions the mixing chamber can be easily charged with the inhalable pulverulent carrier substance for preparing the dry application of substances, and can be discharged after application without any problems.

In correspondence with another preferred embodiment of the invention a filter array is provided between the cover and the mixing chamber, which filter array presents a structure consisting of a fine filter having a mesh size of roughly 1–3 μm, preferably in the form of a cellulose filter, and a supporting filter having a high strength and a mesh size between 50 and 500 μm, preferably in the form of a metal sheet. The fine filter expediently prevents the escape of powder from the mixing chamber and is protected from tearing by the supporting filter which contacts the fine filter on the side facing the vacuum pump.

According to another embodiment of the invention the aerosol generator is provided for producing a particle size of <0.5 μm at a relative moisture of <50%, preferably <30%.

BRIEF DESCRIPTION OF THE DRAWINGS

The invention will now be described in more details in the following with reference to the attached drawing wherein:

FIG. 6 shows a flow chart.

DETAILED DESCRIPTION OF THE PREFERRED EMBODIMENT

Figure 1:
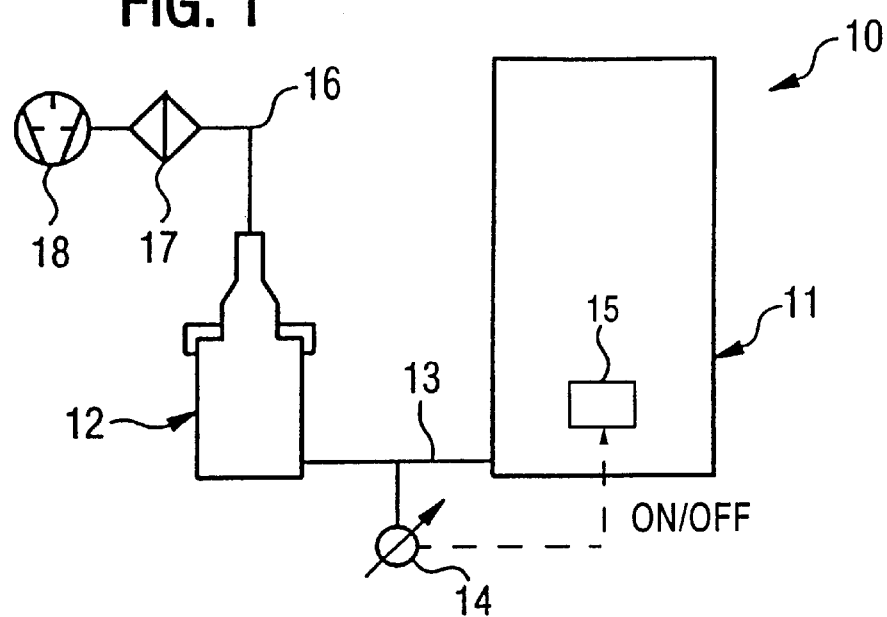
FIG. 1 is a schematic view of various parts of the device.

FIG. 1 shows a schematic view of one embodiment of the inventive device 10. The device 10 according to FIG. 1 consists of an aerosol generator 11 and a mixing chamber 12 connected to the aerosol generator 11 via a connecting line 13 for introducing dried aerosol particles into the mixing chamber 12. A moisture sensor 14 is inserted into the line 13, which serves to measure the moisture of the dried aerosol particles and which is suitable to turn a conventional nozzle-type vaporization 15 in the aerosol generator 11 on and off for the individual adjustment of the moisture level, as indicated by the dotted line.

At the upper end of the mixing chamber a line 16 is connected which leads via a filter array 17 to a vacuum pump 18.

Figure 2:
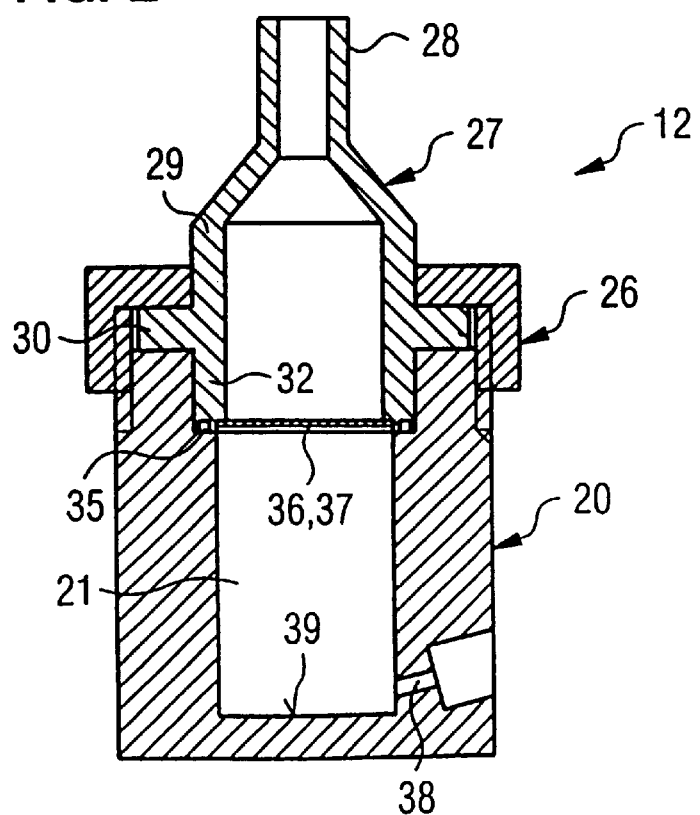
FIG. 2 is a vertical section taken through a configuration of the mixing chamber.

FIG. 2 shows a mixing chamber 12 modified versus relative to FIG. 1, which is illustrated in a vertical section. The variation from the mixing chamber according to FIG. 1 consists in the aspect that the filter array 17 is arranged in the region of the outlet of the mixing chamber, as will be explained in more details below. The mixing chamber 12 according to FIGS. 2 and 3 consists of a hollow cylindrical body 20 with the actual chamber for receiving the pulverulent carrier substance and for whirling being formed inside this body. The lower side of the body 20 is closed. The body 20 is open at the top, as may be seen with reference to FIG. 3, while the cylindrical interior space 21 flares via a radial shoulder section 22 towards an open inserting section 22 having a larger diameter. In the region of the inserting section 22 an outside threading 24 is provided on the body 20, onto which an inside threading 25 of a swivel nut 26 is screwed, as is shown in FIG. 2.

The reference numeral 27 denote a hollow cover which comprises an aspiration connector 28 for the vacuum pump 18 on its upper side, which connector is conically flaring towards a hollow cylindrical section 29 having a radial bearing flange 30 for support on the surface 31 on the upper side of the body 20. Below the flange 30, an inserting section 32 is formed which opens into a radial bearing surface 33 for the shoulder 23, as is shown in FIG. 2. A groove 34 is provided in the surface 33 for receiving an O-ring 35, beside a shoulder-shaped recess of a smaller diameter for receiving a filter array consisting of a supporting filter 36 and a fine filter 37. In the condition of the mixing chamber 12 as assembled the filters 36 and 37 are bearing against each other while the interior space 21 of the body 20 is closed upwards by the adjacent filters 36 and 37. FIG. 2 also shows how the swivel nut 26 rests on the flange 30 of the cover 27 and is screwed by its inside threading 25 onto the outside threading 24 on the body.

Figure 3:
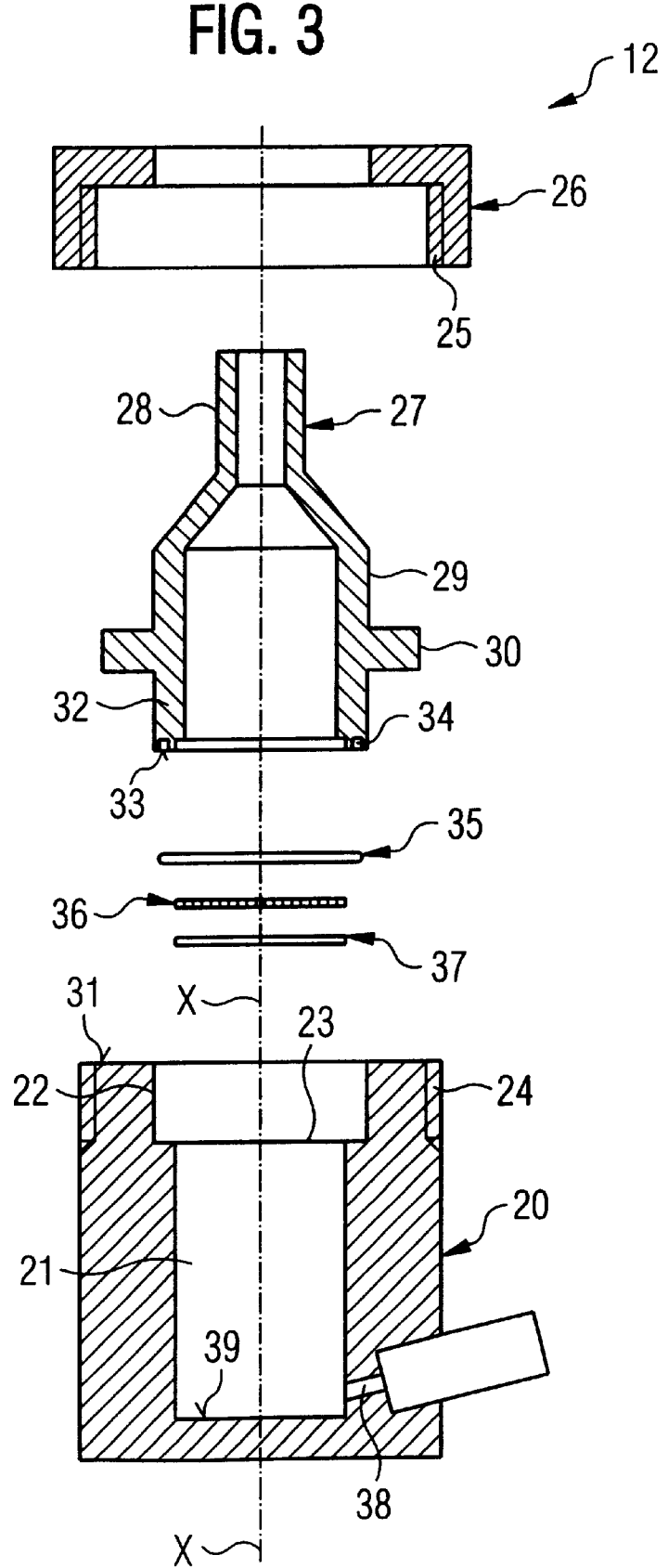
FIG. 3 is an exploded sectional view of the mixing chamber illustrated in FIG. 2.
Figure 4:
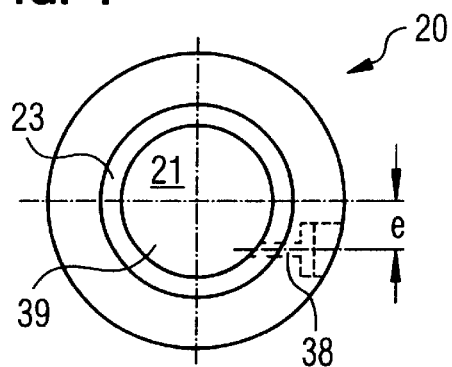
FIG. 4 shows a plan view of the lower part of the mixing chamber illustrated in FIG. 2.

The reference numeral 38 denotes an inlet passage in FIGS. 2 to 4, which, as is evident from FIGS. 2 and 3, is arranged in the lower section of the interior space 21 and is oriented with a downward inclination towards the inner bottom area 39. In the plan view onto the body 20, as illustrated in FIG. 4, it is moreover evident that the inlet opening 38 is disposed with an eccentricity e relative to the vertical axis of symmetry X—X of the body 20. With this provision it is expediently possible to achieve a cyclone-type whirling of the pulverulent carrier substances (not illustrated) contained in the interior space 21 during the introduction of the dry aerosol particles.

Figure 5:
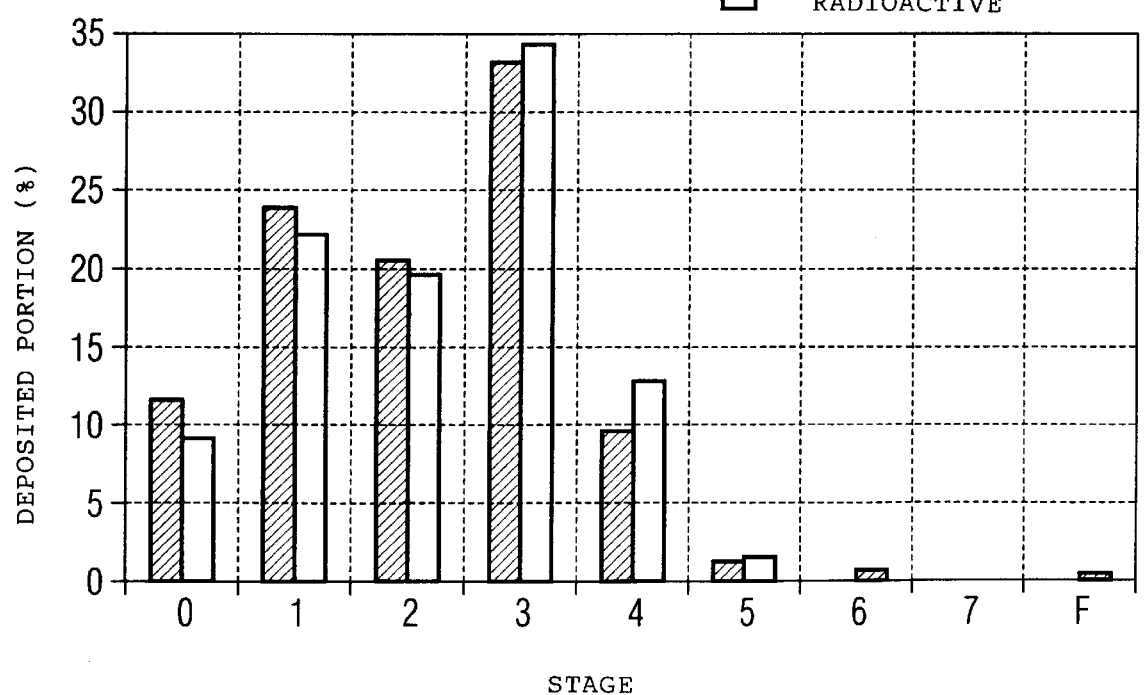
FIG. 5 is a representation of a gravimetrically and radioactively measured particle distribution.

FIG. 5 is a graph representing the particle distribution of a pulverulent carrier substance as measured by means of an Anderson impactor, in a way that a comparison is shown between a gravimetrically measured distribution, indicated in black, and a radioactively measured distribution, indicated in white.

For the realization of these measurements initially sodium pertechnetate particles were deposited with porous aerosol particles consisting of albumin, DPPC and estradiol. A quantity between 5 and 50 mg of the dry porous particles was charged into the mixing chamber. Between 25% and 45% of a vaporized quantity of 10 MBq$^{99m}$Tc arrived at the porous particles. The distribution of the particle sizes in a representative sample of the particles was measured prior to and after marking by means of a 9-stage impactor, with the distribution of the particle sizes being studied both by gravimetry (the particles at each stage of the impactor were weighed by means of micro scales) and by measurement of the radioactivity.

The distribution measured with both measuring methods is illustrated in FIG. 2. A significant distinction between the distribution established by gravimetry and the distribution established by radioactivity cannot be recognized. This leads to the result that the marking does not take any influence on the powder particles and that the marking correctly reflects the distribution of the particle sizes in the aerosol.

What is claimed is:

1. Method of dry application of at least one of a marker and an active substance, on an inhalable pulverulent carrier substance, comprising the following steps:

(a) dissolving the substance to be applied in a liquid;

(b) vaporizing the liquid and subsequently drying aerosol droplets for producing aerosol particles; and (c) establishing a whirling contact of the aerosol particles with said pulverulent carrier substance.

2. Method according to claim 1 wherein prior to step (c) a moisture content of said aerosol particles is checked.

3. Method according to claim 2, wherein the moisture content of said aerosol particles is adapted to the respective carrier substance.

4. Method according to claim 1, wherein the establishment of said whirling contact is realized by aspiration of circulated aerosol particles through said carrier substance.

5. Method according to claim 4, wherein the aspiration of said aerosol particles through said current substance is performed via a retaining filter array.

6. Device for dry application of at least one of a marker and active substance, on inhalable pulverulent carrier substances, comprising:

an aerosol generator for receiving the substance to be applied as dissolved in a liquid and for forming aerosol particles of the substance; a drying means for drying the aerosol particles so formed; and a mixing chamber for receiving the pulverulent carrier substance and for adheringly contacting said substance with said dry aerosol particles by whirling with dry aerosol particles circulated and introduced therein from the aerosol generator.

7. Device according to claim 6, wherein for the introduction of dry aerosol particles and for whirling in said mixing chamber a vacuum pump is provided which is connected to said mixing chamber via a filter array.

8. Device according to claim 6, wherein said mixing chamber is defined by a vertical axis an inlet eccentric with respect to said vertical axis for said aerosol particles.

9. Device according to claim 8, wherein said inlet is provided in the lower region of said mixing chamber with an oblique downward orientation with respect to said vertical axis.

10. Device according to claim 6, wherein for checking the moisture of said dried aerosol particles a moisture sensor is provided.

11. Device according to claim 10, wherein said moisture sensor is arranged in a connecting line between said aerosol generator and said mixing chamber.

12. Device according to claim 10, wherein the moisture of said dried aerosol particles can be adjusted for adaptation to the respective carrier substance by means of an on/off operation of said nozzle-type vaporizer in said aerosol generator.

13. Device according to claim 6, wherein said mixing chamber is adapted for being closed and sealed by means of a cover having a connector for connection of a vacuum pump.

14. Device according to claim 13, wherein said cover is adapted for being partly inserted into an upper section of said mixing chamber.

15. Device according to claim 13, wherein said cover is adapted for being fastened by means of a swivel nut on said mixing chamber.

16. Device according to claim 13, wherein a filter array is disposed between said cover and said mixing chamber.

17. Device according to claim 16, wherein said filter array has a structure composed of a fine filter having a mesh size of roughly 1–3 µm and a high-strength supporting filter having a mesh size between roughly 50 and 500 mm.

18. Device according to claim 17, wherein said fine filter consists of a cellulose filter, and that said supporting filter is formed with a metal sheet.

19. Device according to claim 6, wherein said aerosol generator is provided for producing a particle size of <0.5 µm at a relative moisture of <50%.

20. Device according to claim 10, wherein a hygrometer is provided as moisture sensor.

21. Device according to claim 6, wherein said aerosol generator is a nozzle-type.

22. Device according to claim 6, wherein said aerosol generator is an ultrasonic-type.

\* \* \* \* \*